(12) United States Patent
Hyde et al.

(10) Patent No.: US 8,114,346 B2
(45) Date of Patent: Feb. 14, 2012

(54) EVENT-TRIGGERED ULTRAVIOLET LIGHT STERILIZATION OF SURFACES

(75) Inventors: Roderick A. Hyde, Redmond, WA (US); Muriel Y. Ishikawa, Livermore, CA (US); Jordin T. Kare, Seattle, WA (US); Elizabeth A. Sweeney, Seattle, WA (US); Lowell L. Wood, Jr., Bellevue, WA (US); Victoria Y. H. Wood, Livermore, CA (US)

(73) Assignee: The Invention Science Fund I, LLC

( * ) Notice: Subject to any disclaimer, the term of this patent is extended or adjusted under 35 U.S.C. 154(b) by 718 days.

(21) Appl. No.: 12/231,676

(22) Filed: Sep. 3, 2008

(65) Prior Publication Data
US 2009/0117001 A1    May 7, 2009

Related U.S. Application Data

(63) Continuation-in-part of application No. 12/218,214, filed on Jul. 11, 2008, now Pat. No. 8,029,740, and a continuation-in-part of application No. 11/894,031, filed on Aug. 17, 2007.

(51) Int. Cl.
*A61L 2/10* (2006.01)
(52) U.S. Cl. .......... 422/24; 422/22; 422/292; 250/492.1
(58) Field of Classification Search ............. 422/22, 422/24, 28, 292, 300; 250/492.1, 492.3
See application file for complete search history.

(56) References Cited

U.S. PATENT DOCUMENTS

| | | | |
|---|---|---|---|
| 2,602,724 A | 7/1952 | Batchelor | |
| 3,314,746 A * | 4/1967 | Millar | 422/186 |
| 4,296,068 A | 10/1981 | Hoshino | |
| 4,598,579 A | 7/1986 | Cummings et al. | |
| 4,788,975 A | 12/1988 | Shturman et al. | |
| 5,000,731 A | 3/1991 | Wong et al. | |
| 5,155,707 A | 10/1992 | Fisher | |
| 5,156,839 A | 10/1992 | Pennell et al. | |
| 5,164,164 A | 11/1992 | Strickler et al. | |
| 5,326,567 A | 7/1994 | Capelli | |
| 5,367,720 A | 11/1994 | Stephens et al. | |
| 5,607,683 A | 3/1997 | Capelli | |
| 5,622,848 A | 4/1997 | Morrow | |
| 5,630,379 A | 5/1997 | Gerk et al. | |
| 5,704,352 A | 1/1998 | Tremblay et al. | |
| 5,733,270 A | 3/1998 | Ling et al. | |
| 5,771,528 A | 6/1998 | Nappi, Sr. | |
| 5,820,821 A | 10/1998 | Kawagoe et al. | |

(Continued)

FOREIGN PATENT DOCUMENTS

WO    WO 91/06855 A2    5/1991
(Continued)

OTHER PUBLICATIONS

U.S. Appl. No. 12/315,884, Boyden et al.
(Continued)

*Primary Examiner* — Sean E Conley (57) ABSTRACT

Solutions for limiting the undesirable spread of pathogens by indirect contact are provided. The solutions involve event-controlled self-sterilization of contact regions on articles or fixtures. A self-sterilizing article structure, in response to a contact event, allows sterilizing UV energy to controllably flow from a UV generator within the article to a portion of the contact region.

54 Claims, 6 Drawing Sheets

U.S. PATENT DOCUMENTS

| | | | |
|---|---|---|---|
| 5,993,382 | A | 11/1999 | Pruitt, Sr. |
| 6,135,990 | A | 10/2000 | Heller et al. |
| 6,304,786 | B1 | 10/2001 | Heil, Jr. et al. |
| 6,348,042 | B1 | 2/2002 | Warren, Jr. |
| 6,350,263 | B1 | 2/2002 | Wetzig et al. |
| 6,426,066 | B1 | 7/2002 | Najafi et al. |
| 6,443,147 | B1 | 9/2002 | Matter |
| 6,451,003 | B1 | 9/2002 | Prosl et al. |
| 6,461,569 | B1 | 10/2002 | Boudreaux |
| 6,478,778 | B1 | 11/2002 | Jacobsen et al. |
| 6,488,704 | B1 | 12/2002 | Connelly et al. |
| 6,506,416 | B1 | 1/2003 | Okauchi et al. |
| 6,585,677 | B2 | 7/2003 | Cowan, Jr. et al. |
| 6,675,425 | B1 * | 1/2004 | Iimura ............... 15/105 |
| 6,730,113 | B2 | 5/2004 | Eckhardt et al. |
| 6,743,190 | B2 | 6/2004 | Connelly et al. |
| 6,750,055 | B1 | 6/2004 | Connelly et al. |
| 6,789,183 | B1 | 9/2004 | Smith et al. |
| 6,793,642 | B2 | 9/2004 | Connelly et al. |
| 6,831,748 | B2 | 12/2004 | Tittel et al. |
| 6,913,589 | B2 | 7/2005 | Dextradeur et al. |
| 6,914,279 | B2 | 7/2005 | Lu et al. |
| 6,932,787 | B2 | 8/2005 | Cowan et al. |
| 6,960,201 | B2 | 11/2005 | Cumbie |
| 6,980,716 | B1 | 12/2005 | Diaz et al. |
| 7,118,548 | B2 | 10/2006 | Børgesen |
| 7,143,709 | B2 | 12/2006 | Brennan et al. |
| 7,151,139 | B2 | 12/2006 | Tiller et al. |
| 7,160,931 | B2 | 1/2007 | Cheng et al. |
| 7,183,048 | B2 | 2/2007 | Felkner et al. |
| 7,195,608 | B2 | 3/2007 | Burnett |
| 7,217,425 | B2 | 5/2007 | Serhan et al. |
| 7,226,441 | B2 | 6/2007 | Kulessa |
| 7,232,429 | B2 | 6/2007 | Moreci |
| 7,236,821 | B2 | 6/2007 | Cates et al. |
| 7,238,363 | B2 | 7/2007 | Mansouri et al. |
| 7,244,232 | B2 | 7/2007 | Connelly et al. |
| 7,253,152 | B2 | 8/2007 | Panero et al. |
| 7,276,255 | B2 | 10/2007 | Selkon |
| 7,288,232 | B2 | 10/2007 | Morrow et al. |
| 7,306,620 | B2 | 12/2007 | Cumbie |
| 7,309,330 | B2 | 12/2007 | Bertrand et al. |
| 7,334,594 | B2 | 2/2008 | Ludin |
| 7,345,372 | B2 | 3/2008 | Roberts et al. |
| 7,348,021 | B2 | 3/2008 | Klein |
| 7,354,575 | B2 | 4/2008 | Shachar et al. |
| 7,390,310 | B2 | 6/2008 | McCusker et al. |
| 7,396,676 | B2 | 7/2008 | Robotti et al. |
| 7,442,372 | B2 | 10/2008 | Kakkis |
| 7,524,298 | B2 | 4/2009 | Gharib et al. |
| 7,535,692 | B2 | 5/2009 | Krupenkin et al. |
| 7,570,018 | B2 | 8/2009 | Waguespack |
| 7,598,501 | B2 * | 10/2009 | Jones ............... 250/455.11 |
| 2002/0182262 | A1 | 12/2002 | Selkon |
| 2003/0017073 | A1 | 1/2003 | Eckhardt et al. |
| 2004/0208940 | A1 | 10/2004 | Selkon |
| 2004/0253138 | A1 | 12/2004 | Malak |
| 2005/0142157 | A1 | 6/2005 | Alimi |
| 2005/0164169 | A1 | 7/2005 | Malak |
| 2005/0203495 | A1 | 9/2005 | Malak |
| 2005/0288654 | A1 | 12/2005 | Nieman et al. |
| 2006/0004317 | A1 | 1/2006 | Mauge et al. |
| 2006/0020239 | A1 | 1/2006 | Geiger et al. |
| 2007/0074672 | A1 | 4/2007 | Torgerson et al. |
| 2007/0173755 | A1 | 7/2007 | Alimi et al. |
| 2007/0176117 | A1 | 8/2007 | Redmond et al. |
| 2007/0196357 | A1 | 8/2007 | Alimi et al. |
| 2007/0207073 | A1 | 9/2007 | Drucker |
| 2007/0249969 | A1 | 10/2007 | Shields, Jr. |
| 2007/0274909 | A1 | 11/2007 | Justel et al. |
| 2007/0276208 | A1 | 11/2007 | Connelly et al. |
| 2008/0033519 | A1 | 2/2008 | Burwell et al. |
| 2008/0039768 | A1 | 2/2008 | Francis |
| 2008/0051691 | A1 | 2/2008 | Dragoon et al. |
| 2008/0051736 | A1 | 2/2008 | Rioux et al. |
| 2008/0056933 | A1 | 3/2008 | Moore et al. |
| 2008/0058798 | A1 | 3/2008 | Wallace et al. |
| 2008/0095977 | A1 | 4/2008 | Aizenberg et al. |
| 2008/0223717 | A1 | 9/2008 | Isaksson et al. |
| 2008/0234786 | A1 | 9/2008 | Cumbie |
| 2008/0248993 | A1 | 10/2008 | Hannappel et al. |
| 2008/0253712 | A1 | 10/2008 | Allen et al. |
| 2008/0265179 | A1 | 10/2008 | Havens et al. |
| 2009/0054824 | A1 | 2/2009 | Melsheimer et al. |
| 2009/0054827 | A1 | 2/2009 | Eide |
| 2009/0110711 | A1 | 4/2009 | Trollsas et al. |
| 2009/0118661 | A1 | 5/2009 | Moehle et al. |
| 2009/0185988 | A1 | 7/2009 | Maleski et al. |

FOREIGN PATENT DOCUMENTS

| | | |
|---|---|---|
| WO | WO/92/01222 | 1/1992 |
| WO | WO/97/00586 | 1/1997 |
| WO | WO/00/09733 | 2/2000 |
| WO | WO/00/29613 | 5/2000 |
| WO | WO/00/56185 | 9/2000 |
| WO | WO/01/13926 A2 | 3/2001 |
| WO | WO/01/54704 A1 | 8/2001 |
| WO | WO/02/102421 A1 | 12/2002 |
| WO | WO/2004/027116 A2 | 4/2004 |
| WO | WO/2004/031077 A2 | 4/2004 |
| WO | WO/2005/100100 A1 | 10/2005 |
| WO | WO/2005/117914 A2 | 12/2005 |
| WO | WO/2006/044324 A2 | 4/2006 |
| WO | WO/2007/070801 A3 | 6/2007 |
| WO | WO/2007/085021 A3 | 7/2007 |
| WO | WO/2008/020770 A1 | 2/2008 |
| WO | WO/2008/073774 A1 | 6/2008 |
| WO | WO/2008/083390 A2 | 10/2008 |

OTHER PUBLICATIONS

U.S. Appl. No. 11/973,367, Hyde et al.

U.S. Appl. No. 11/973,357, Hyde et al.

Bozhevolnyi, Sergey I. et al.; "Photonic bandgap structures for long-range surface plasmon polaritons"; Optics Communications; bearing a date of 2005; pp. 328-333; vol. 250; Elsevier B.V.

ESR European Search Report; European App. No. EP 08 25 1153; Dec. 15, 2008; p. 1.

PCT International Search Report; International App. No. PCT/US 09/04028; Sep. 10, 2009; pp. 1-2.

Albert, Richard K. and Condie, Frances; "Medical Intelligence: Hand-Washing Patterns in Medical Intensive-Care Units"; New England Journal of Medicine; Jun. 1981; pp. 1465-1466; vol. 304, No. 24.

U.S. Appl. No. 11/973,010, Hyde et al.

Aarabi, Shahram et al.; "Research in Translation: Hypertrophic Scar Formation Following Burns and Trauma: New Approaches to Treatment"; PLoS Medicine; Sep. 2007; pp. 1464-1470; vol. 4, Issue 9, No. e234; located at: www.plosmedicine.org.

Abdollahi, Amir; "Apoptosis Signals in Lymphoblasts Induced by Focused Ultrasound"; The FASEB Journal—FJ Express; Sep. 2004; pp. 1413-1414; vol. 18; FASEB.

"Arglaes® Controlled-Release Silver Technology"; Medline; 2003; 6 pages; Medline Industries, Inc.; located at: www.medline.com.

Ashush, Hagit et al.; "Apoptosis Induction of Human Myeloid Leukemic Cells by Ultrasound Exposure"; Cancer Research; bearing a date of Feb. 15, 2000; pp. 1014-1020; vol. 60.

Brogden, Kim A.; "Antimicrobial Peptides: Pore Formers or Metabolic Inhibitors in Bacteria?"; Nature Reviews, Microbiology; Mar. 2005; pp. 238-250; vol. 3.

Carcillo, Joseph A. et al.; "Early Markers of Infection and Sepsis in Newborns and Children"; Leading Article, Advances in Sepsis; 2006; pp. 118-125; vol. 5, No. 4.

Caricchio, Roberto et al.; "Ultraviolet B Radiation-Induced Cell Death: Critical Role of Ultraviolet Dose in Inflammation and Lupus Autoantigen Redistribution"; The Journal of Immunology; 2003; pp. 5778-5786; vol. 171; The American Association of Immunologists, Inc.

Chen, Ting-Hsuan et al.; "A Wettability Switchable Surface Driven by Electrostatic Induced Surface Morphology Change Without Energy Interference on Reagents in Droplets"; MEMS; Jan. 2006; pp. 178-181; IEEE.

Cheng, Gang et al.; "Switchable Polymer Surfaces: A Switchable Biocompatible Polymer Surface with Self-Sterilizing and Nonfouling Capabilities"; Angewandte Chemie; 2008; pp. 8831-8834; vol. 47; Wiley-VCH Verlag GmbH & Co.

De Fabo, Edward C.; "Advances in Brief: Ultraviolet B but not Ultraviolet A Radiation Initiates Melanoma"; Cancer Research; bearing a date of Sep. 15, 2004; pp. 6372-6376; vol. 64; American Association for Cancer Research.

Donlan, R. M. et al.; "Model Systems for Growing and Quantifying *Streptococcus pneumoniae* Biofilms In Situ and in Real Time"; Applied and Environmental Microbiology; Aug. 2004; pp. 4980-4988; vol. 70, No. 8; American Society for Microbiology.

"Fact Sheet: Cerebrospinal Fluid Shunt Systems for the Management of Hydrocephalus"; Hydrocephalus Association; 2000; 7 pages; Hydrocephalus Association; located at: www.hydroassoc.org.

Feng, Xinjian et al.; "Reversible Super-Hydrophobicity to Super-Hydrophilicity Transition of Aligned ZnO Nanorod Films"; JACS Communications; 2004; pp. 62-63; vol. 126; American Chemical Society.

Feng, Yi et al.; "Gastric Cancer: Low Intensity Ultrasound-Induced Apoptosis in Human Gastric Carcinoma Cells"; World Journal of Gastroenterology; bearing a date of Aug. 21, 2008; pp. 4873-4879; vol. 14, No. 31; The WJG Press; located at: www.wjgnet.com.

Fogh-Andersen, Niels et al.; "Composition of Interstitial Fluid"; General Clinical Chemistry; 1995; pp. 1522-1525; vol. 41, No. 10.

Forbes, Peter; "Scientific American: Self-Cleaning Materials: Lotus Leaf-Inspired Nanotechnology"; Scientific American Magazine; bearing a date of Jul. 30, 2008; pp. 1-5; printed on Nov. 21, 2008.

Goclawski, Jaroslaw et al.; "The Measurement of Wetting Angle by Applying and ADSA Model of Sessile Drop on Selected Textile Surfaces"; Fibres and Textiles in Eastern Europe; Apr./Jun. 2008; pp. 84-88; vol. 16, No. 2(67).

Grunfeld, Carl; "Lipids, Lipoproteins, Triglyceride Clearance, and Cytokines in Human Immunodeficiency Virus Infection and the Acquired Immunodeficiency Syndrome"; Journal of Clinical Endocrinology and Metabolism; 1992; pp. 1045-1052; vol. 74, No. 5; The Endocrine Society.

Imam, S.K. et al.; "Radiotracers for Imaging of Infection and Inflammation—A Review"; World Journal Nuclear Medicine.; Jan. 2006; pp. 40-55; vol. 5, No. 1.

"Introduction to ORP as the Standard of Postharvest Water Disinfection Monitoring"; UC Davis, Vegetable Research and Information Center; pp. 1-4.

Killer, H. E. et al.; "The Optic Nerve: A New Window into Cerebrospinal Fluid Composition?"; Brain; 2006; pp. 1027-1030; vol. 129.

Lahann, Joerg; "A Reversibly Switching Surface"; Reports, Science; bearing a date of Jan. 17, 2003; pp. 371-374 (plus Erratum); vol. 299; located at: www.sciencemag.org.

Lepock, James R.; "Cellular Effects of Hyperthermia: Relevance to the Minimum Dose for Thermal Damage"; International Journal of Hyperthermia, Taylor & Francis healthsciences; May-Jun. 2003; pp. 252-266; Vol. 19, No. 3; Taylor & Francis Ltd.

Lin, Yi-Hsin; "Electrically Tunable Wettability of Liquid Crystal/Polymer Composite Films"; Optics Express; bearing a date of Oct. 27, 2008; pp. 17591-17598; Vol. 16, No. 22; OSA.

Masteikova, Ruta et al.; "Stimuli-Sensitive Hydrogels in Controlled and Sustained Drug Delivery"; Medicina; 2003; pp. 19-24; vol. 39, No. 2.

McKenna, Susan M. et al.; "The Inhibition of Bacterial Growth by Hypochlorous Acid"; Biochemistry; 1988; pp. 685-692; vol. 254.

Nejat, Farideh et al.; "Original Article: A Randomized Trial of Ceftriaxone Versus Trimethoprimsulfamethoxazole to Prevent Ventriculoperitoneal Shunt Infection"; Journal of Microbiology, Immunology and Infection; 2008; pp. 112-117; vol. 41; Journal of Microbiology, Immunology and Infection.

Ng, P C; "Review: Diagnostic Markers of Infection in Neonates"; Arch Dis Child Fetal Neonatal Ed; 2004; pp. F229-F235; vol. 89; located at: www.archdischild.com.

Okada, Ayako et al.; "Inhibition of Biofilm Formation Using Newly Developed Coating Materials with Self-Cleaning Properties"; Dental Materials Journal; 2008; pp. 565-572; vol. 27, No. 4.

Piper, Kerryl E. et al.; "Mist Ultrasound Therapy Device Removal of In Vitro Bacterial Biofilms"; Mayo Clinic.

Rathmell, James P. et al.; "Infectious Risks of Chronic Pain Treatments: Injection Therapy, Surgical Implants, and Intradiscal Techniques"; Regional Anesthesia and Pain Medicine; 2006; pp. 346-352; vol. 31, No. 4.

Rediske, Andrea M. et al.; "Pulsed Ultrasound Enhances the Killing of *Escherichia coli* Biofilms by Aminoglycoside Antibiotics In Vivo"; Antimicrobial Agents and Chemotherapy; Mar. 2000; pp. 771-772; vol. 44, No. 3; American Society for Microbiology; downloaded on Aug. 24, 2009.

Reid, Marvin et al.; "The Acute-Phase Protein Response to Infection in Edematous and Nonedematous Protein-Energy Malnutrition"; The American Journal of Clinical Nutrition; 2002; pp. 1409-1415; vol. 76; American Society for Clinical Nutrition.

Roti Roti, Joseph L.; "Review: Cellular Responses to Hyperthermia (40-46° C): Cell Killing and Molecular Events"; Informa healthcare; Feb. 2008; pp. 3-15; vol. 24, No. 1; Informa UK Ltd.

Seehusen, Dean A. et al.; "Cerebrospinal Fluid Analysis"; American Family Physician; bearing a date of Sep. 15, 2003; pp. 1103-1108; vol. 68, No. 6; located at: www.aafg.org/afp.

Setroikromo, R.; "Heat Shock Proteins and Bcl-2 Expression and Function in Relation to the Differential Hyperthermic Sensitivity between Leukemic and Normal Hematopoietic Cells"; Cell Stress & Chaperones; 2007; pp. 320-330; vol. 12, No. 4; Cell Stress Society International.

"SilvaSorb® Targeted Antimicrobial Protection"; Medline; 2005; 16 pp.; Medline Industries Inc.; located at www.medline.com.

Sodja, Caroline; "Splenic T Lymphocytes Die Preferentially During Heat-Induced Apoptosis: NuMA Reorganization as a Marker"; Journal of Cell Science; 1998; pp. 2305-2313; vol. 111; The Company of Biologists Limited.

Stankiewicz, Adam R.; "Hsp70 Inhibits Heat-Induced Apoptosis Upstream of Mitochondria by Preventing Bax Translocation"; The Journal of Biological Chemistry; Bearing a date of Nov. 18, 2005; pp. 38729-38739; vol. 280, No. 46; The American Society for Biochemistry and Molecular Biology, Inc.

"Study E: Comparison of the Moisture Uptake and Retention Properties of Biopatch® and SilvaSorb Site®"; 2 pages.

Tuteja, Anish et al.; "Robust Omniphobic Surfaces"; PNAS; bearing a date of Nov. 25, 2008; pp. 18200-18205; vol. 105, No. 47; The National Academy of Sciences of the USA.

Wang, Shutao; "Review: Photoresponsive Surfaces with Controllable Wettability"; Journal of Photochemistry and Photobiology C: Photochemistry Review, Science Direct; 2007; pp. 18-29; vol. 8; Elsevier B.V.

Wang, Zhe et al.; "APD: The Antimicrobial Peptide Database"; Nucleic Acids Research; 2004; pp. D590-D592; vol. 32; Oxford University Press.

Watson, Mark A.; "Review: Clinical Utility of Biochemical Analysis of Cerebrospinal Fluid"; Clinical Chemistry; 1995; pp. 343-360; vol. 41, No. 3.

Wentworth, Jr., Paul et al.; "Reports: Evidence for Antibody-Catalyzed Ozone Formation in Bacterial Killing and Inflammation"; Science AAAS; 2002; pp. 2195-2199; vol. 298; downloaded on Jul. 14, 2009; located at: www.sciencemag.org.

Zhong, Yinghui et al.; "Review: Biomaterials for the Central Nervous System"; Journal of the Royal Society Interface; 2008; pp. 957-975; vol. 5; The Royal Society.

European Search Report; European App. No. EP 08 25 1153; Jul. 10, 2009; pp. 1-2.

* cited by examiner

EVENT-TRIGGERED ULTRAVIOLET LIGHT STERILIZATION OF SURFACES

CROSS-REFERENCE TO RELATED APPLICATIONS

The present application is related to and claims the benefit of the earliest available effective filing date from the following listed application(s).

RELATED APPLICATION

1. For purposes of the USPTO extra-statutory requirements, the present application constitutes a continuation-in-part of U.S. patent application Ser. No. 12/218,214, entitled EVENT-TRIGGERED SELF-STERILIZATION OF ARTICLE SURFACES, naming Roderick A. Hyde, Muriel Y. Ishikawa, Jordin T. Kare, Elizabeth A. Sweeney and Lowell L. Wood, Jr., as inventors, filed Jul. 11, 2008, now U.S. Pat. No. 8,029,740.

2. For purposes of the USPTO extra-statutory requirements, the present application constitutes a continuation-in-part of U.S. patent application Ser. No. 11/894,031, entitled SELF-STERILIZING DEVICE, naming Ralph G. Dacey, Jr., Roderick A. Hyde, Muriel Y. Ishikawa, Eric C. Leuthardt, Nathan P. Myhrvold, Dennis J. Rivet, Michael A. Smith, Clarence T. Tegreene, Lowell L. Wood, Jr., Victoria Y. H. Wood, as inventors, filed Aug. 17, 2007, which is currently co-pending.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present applicant entity has provided above a specific reference to the application(s) from which priority is being claimed as recited by statute. Applicant entity understands that the statute is unambiguous in its specific reference language and does not require either a serial number or any characterization, such as "continuation" or "continuation-in-part," for claiming priority to U.S. patent applications. Notwithstanding the foregoing, applicant entity understands that the USPTO's computer programs have certain data entry requirements, and hence applicant entity is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

BACKGROUND

Diseases and infections can be transmitted by indirect contact. Any contact surface, which is touched by more than one person, can be a transfer point for harmful germs spreading diseases and infections through a population. An example is the common cold. A person, who has a cold, can leave cold virus behind on a door handle he or she touches. A non-infected person, who later touches the door handle, can pick up the cold virus from the door handle and catch the same cold.

For certain high risk environments (e.g., restrooms, food service and health care facilities), public health programs recommend hand washing or hand rubbing routines for maintaining good hand hygiene to prevent or reduce propagation of communicable diseases and infections. However, time and facilities constraints present are major obstacles to maintaining good hand hygiene. Many studies of nosocomial infections show that hand washing protocols are not properly followed even by health care providers. General compliance rates of health care providers with hospital-recommended hand washing or hand rubbing protocols are low. The poor compliance rates have been attributed in part to a lack of knowledge of when and how to clean or disinfect hands, and in part to time constraints and poor access to hand washing facilities or hand rubbing products. (See e.g., Albert R. K., Condie F., NEJM 1981; 304(24):1465-6).

The time and facilities constraints that impede good hand hygiene in hospital environments are even more severe obstacles for achieving good hand hygiene in other public environments. For example, it is not practical to provide hand washing facilities at every door knob or entrance in a working office building, or at every turnstile or contact surface in a bus or train terminal. Further, even where hand washing facilities are provided (e.g., in restrooms), hand washing can be counterproductive. A person, after washing hands, could pick up germs by turning a water faucet handle off, or touching a restroom exit door handle.

Consideration is now being given to other solutions for limiting the undesirable spread of pathogens by indirect contact. Some such solutions may avoid, for example, the time and facilities constraints that hinder solutions that rely on voluntary hand washing by individuals.

SUMMARY

Approaches to limiting the spread of pathogens, for example, by indirect contact are provided.

One approach utilizes self-sterilizing articles using ultraviolet light or radiation ("UV energy"). A self-sterilizing article may include an exterior contact surface or region disposed on an article body. The article body includes an internal ultraviolet light or radiation generator ("UV generator"). This internal UV generator provides UV energy for sterilizing the exterior contact surface or region to inhibit the spread of germs or pathogens. Sterilizing treatments of the exterior contact surface or region with UV energy may be triggered by specific events (e.g., contact, imminent contact, or lapse of time).

The self-sterilizing article may include may include one or more sensors (e.g., contact sensor, a proximity sensor, a chemical sensor, or a biosensor) which are configured to detect if a contact has occurred or is likely, or if biomaterials are present on the exterior contact surface. Further, the self-sterilizing article may include, or be coupled to, control elements that control, time or regulate the flow of UV energy on to the contact surface in response to events. The control elements may act in response to, for example, sensor information, contact surface activity, and/or other control signals. Additionally, the self-sterilizing article may include, or be coupled to, a power source/receiver, which provides energy for the controlled flow of UV energy to the contact surface. Like the control elements, the power source/receiver may be responsive to sensor information, contact surface activity, and/or control signals. A contact surface status indicator coupled to the structure may display a sterilization condition or state of the contact surface to users.

The foregoing summary is illustrative only and is not intended to be limiting. In addition to the illustrative aspects, embodiments, and features described above, further aspects, embodiments, and features of the solutions will become apparent by reference to the drawings and the following detailed description.

BRIEF DESCRIPTION OF THE FIGURES

In the accompanying drawings.

Throughout the figures, unless otherwise stated, the same reference numerals and characters are used to denote like features, elements, components, or portions of the illustrated embodiments.

DESCRIPTION

In the following description of exemplary embodiments, reference is made to the accompanying drawings, which form a part hereof. It will be understood that embodiments described herein are exemplary, but are not meant to be limiting. Further, it will be appreciated that the solutions described herein can be practiced or implemented by other than the described embodiments. Modified embodiments or alternate embodiments may be utilized, in the sprit and scope of the solutions described herein.

Figure 1:
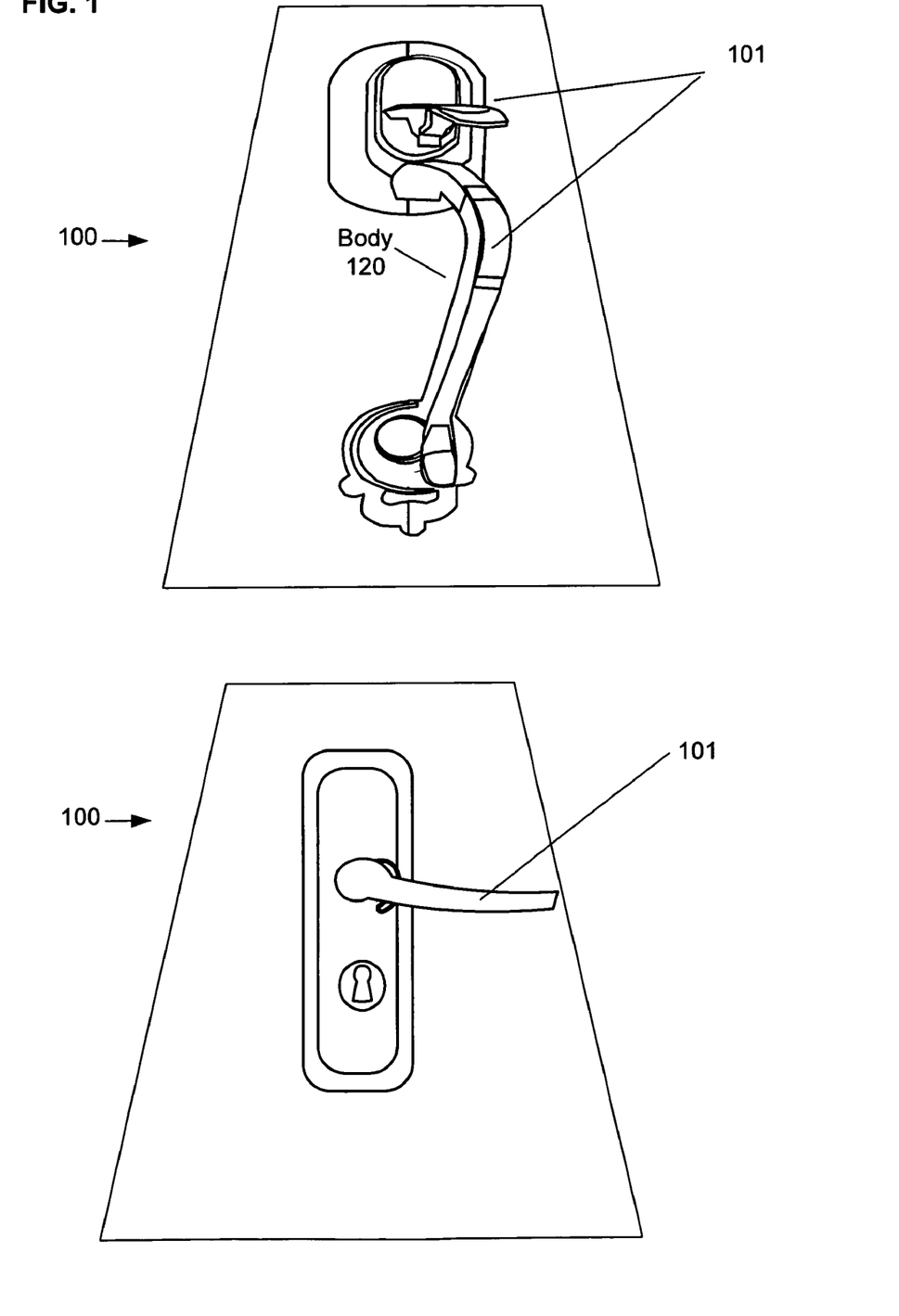
FIG. 1 is a schematic illustration of exemplary self-sterilizing articles or fixtures, which have contact surfaces or regions that are self-sterilized to prevent or reduce the spread of communicable diseases and infections by indirect contact, in accordance with the principles of the solutions described herein.

FIGS. 1-4 show exemplary self-sterilizing articles 100, each having an article body 120 with a contact surface 101 disposed thereon. Exemplary articles 100, as shown for purposes of illustration in FIG. 1, are door handles having particular shapes. Article 100 may, however, be any device or fixture of any shape having one or more surfaces that can be touched or contacted in use. Article 100 may, for example, be a handle, a hand rail, a seat, a key board, a switch, a button, a knob, a computer mouse or control device, a desktop, a bathroom or kitchen or other working surface, a bus seat, a gymnasium apparatus or fixture, a restaurant booth or seat, a toy, a headphone, a telephone, an automatic teller machine, a vending machine, a shopping cart, a household device or fixture, a building device or fixture, an industrial device or fixture, a transport vehicle device or fixture, a medical device or fixture, or any other device or fixture whose contact surfaces are sites for potential transfer of undesirable pathogens amongst users.

Figure 2:
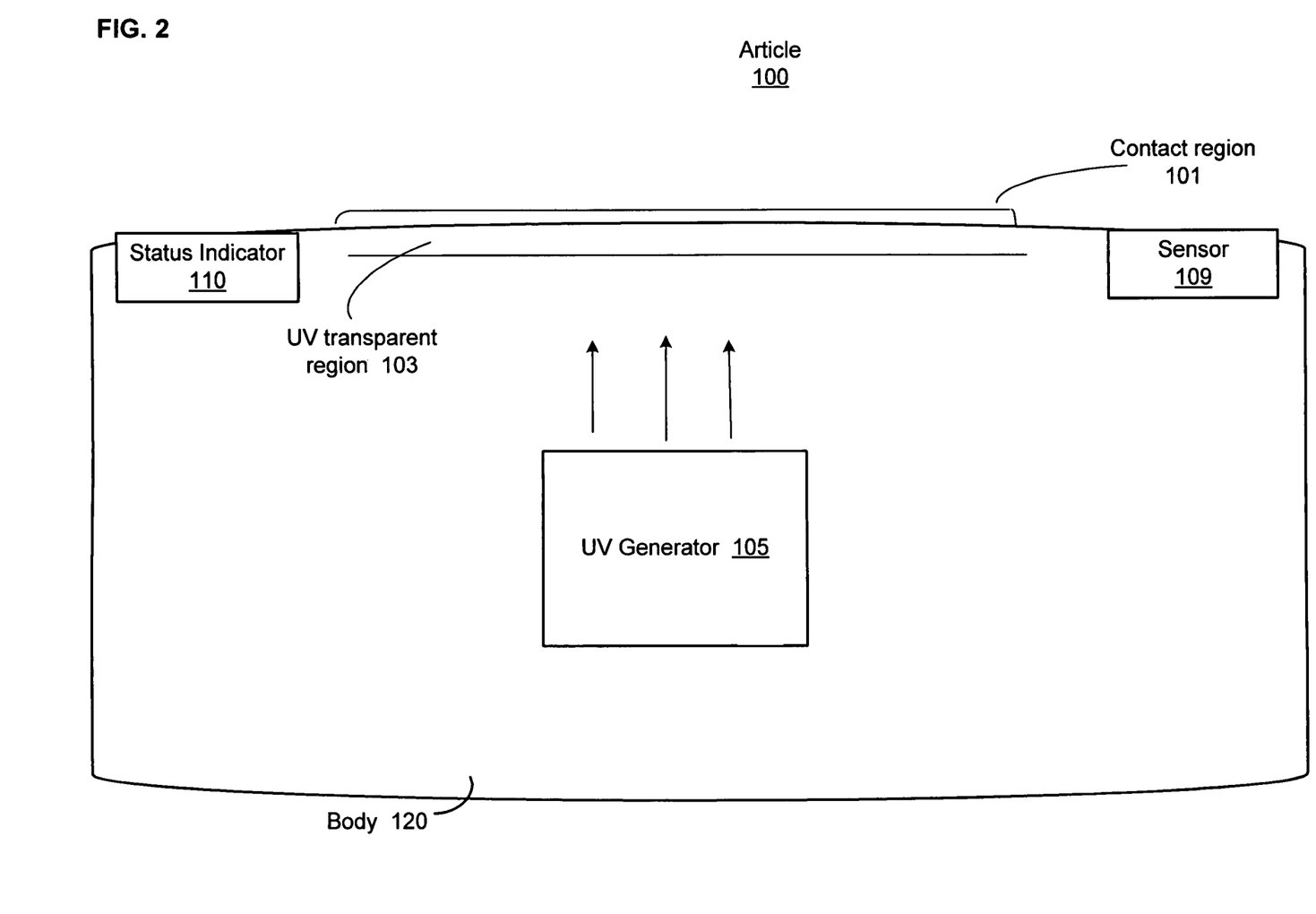
FIG. 2 is a block diagram illustrating an exemplary self-sterilizing article having an external self-sterilizing contact surface and an internal UV energy source, in accordance with the principles of the solutions described herein.

With reference to FIG. 2, self-sterilizing article 100 includes an internal UV source or generator 105, which is arranged to controllably provide UV energy to contact surface 101 from within article body 120. The UV energy may, for example, be applied in "sterilizing" doses, which reduce, disable, or kill pathogens (e.g., bacteria, viruses, or germs) that may be present on contact surface 101. The UV energy may, for example, have frequencies in the UV-C band, which are known to have enhanced germicidal properties over frequencies in other bands. However, it will be understood that the UV energy used in article 100 is not restricted to frequencies in the UV-C band, but may have any suitable frequency or frequencies (e.g., including frequencies in UV-A, and/or UV-B bands) for reducing, disabling or killing pathogens present on contact surface 101. Further, UV generator 105 may be any suitable device generating UV energy at specified frequencies. UV generator 105 may, for example, be a high bandgap semiconductor device, a germicidal lamp, a plasmon-enhanced extreme ultraviolet light source, or a device based on UV-emitting nanostructures, electron-excitable UV-emitting material, or light frequency up-converting material.

In operation, UV energy flows to contact surface 101 from within article 100. For this purpose, article 100 may include a suitable light-guiding structure to transport UV energy from the UV generator 105 to contact region 101. The light-guiding structure may, for example, be configured to transport UV energy from the UV generator to the contact region through an underlying surface region 103. UV energy may, for example, flow from internal UV generator 105 within article 100 to contact surface 101 through an underlying or contiguous region 103, which is at least partially transparent to UV energy. Alternatively or additionally, the light-guiding structure may be configured to laterally transport UV energy from the UV generator to the contact region along a surface of the article body.

Figure 3:
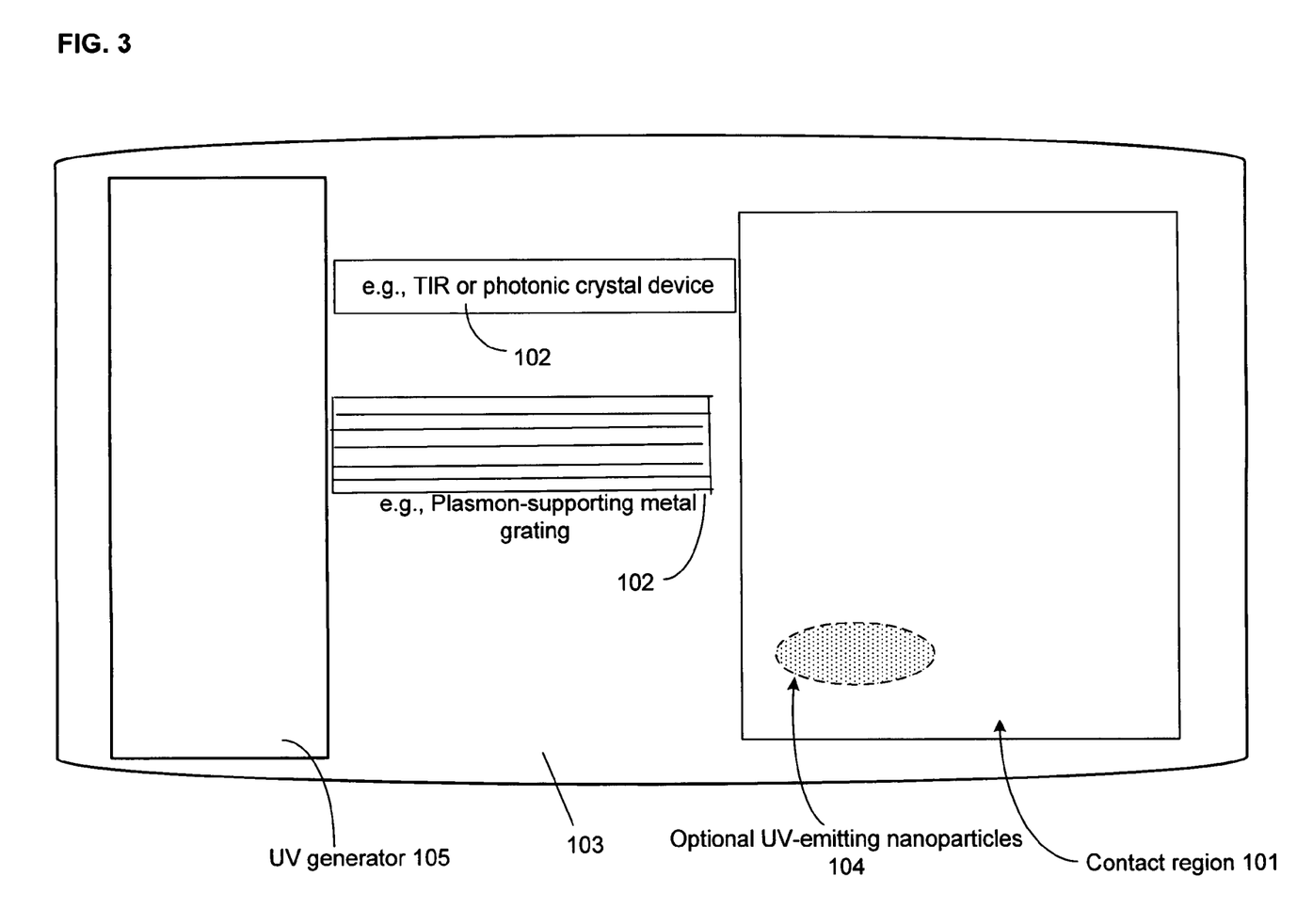
FIG. 3 is a schematic illustration of several optional structures for coupling UV energy to the external self-sterilizing contact surface of FIG. 2, in accordance with the principles of the solutions described herein.

FIG. 3 shows several exemplary light-guiding structures 102 that may be deployed to couple UV energy from internal UV generator 105 to contact surface 101 through an underlying or contiguous region 103. Light-guiding structures 102 may, for example, include a total internal reflection (TIR) device, a photonic crystal device, and/or a plasmon-supporting metal grating structure for coupling UV light generated by the UV generator to the contact region via plasmons.

Figure 4:
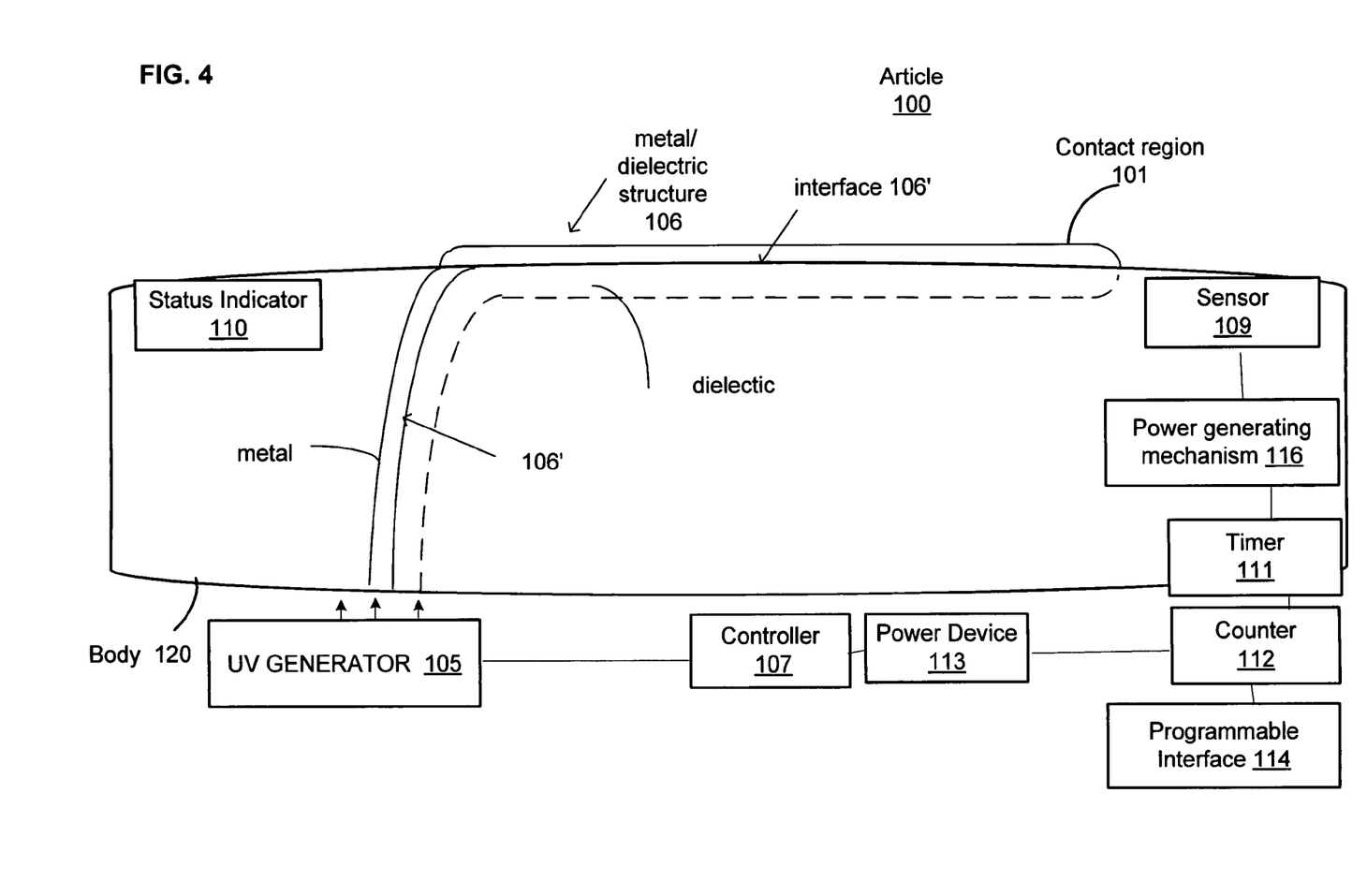
FIG. 4 is a block diagram illustrating an exemplary structure for coupling UV energy via plasmons to the self-sterilizing contact surface, in accordance with the principles of the solutions described herein.

FIG. 4 shows another example of a plasmon-supporting metal/dielectric structure 106 that may be used as light-guiding structure 102. Metal/dielectric structure 106 extends across article body 102. Contact region 101 is formed as an exposed metal portion of metal/dielectric structure 106. In operation, UV energy generated by UV generator 105 may be transferred in the form of plasmons along metal-dielectric interface 106' to contact region 101.

Light-guiding structures 102 may be configured to transport light from the UV generator to the contact region laterally along a surface of the article body (e.g., as shown in FIG. 3) or through the interior of the article body (e.g., as shown in FIGS. 2 and 4).

In some alternate types of self-sterilizing articles 100, UV generator 105 may be spatially integrated with contact region 101 to minimize or dispense with a need to guide UV energy between the two components (105 and 101). In such types of articles, UV generator 105 may be spatially integrated with contact region 101. For example, UV generator 105 may be made of UV-emitting nanostructures, electron-excitable UV-emitting materials, or light frequency up-converting materials, or other materials that can be placed within the contact region itself. FIG. 3 shows, for example, UV-emitting nanoparticles 104 integrated into contact region 101.

Embodiments of UV generator 105/article 100 may include, or operationally interface with, one or more other electrical and/or mechanical components configured to recognize and respond to events, and control the flow of UV energy to contact region 101. For example, with reference to FIGS. 2 and 4, article 100 may optionally include a controller 107, a sensor 109, a status indicator 110, a timer 111, a counter 112, a power source/receiver 113, a power generating mechanism 116, and/or a programmable interface 114. Each of these optional components may be disposed either inside or outside article 100 (see FIG. 4).

Suitable energy or power for operating UV generator 105 may be obtained from an internal or external power source/receiver 113 (e.g., a dry cell or a wound spring or resonant inductive power reception circuitry). Further, operation or movement of article 100 itself may be utilized to generate energy or power for driving UV generator 105 or other components of article 100. For example, contact-induced pressure and/or contact-induced temperature may be utilized to drive or regulate UV generator 105 (e.g., using a pressure- or temperature-activated flow switch).

Additionally or alternatively, article 100 may be coupled to an energy- or power-generating mechanism (e.g., generator 116). Generator 116 may, for example, couple mechanical movement of article 100 (e.g., turning of a door handle, or opening of a door) to drive UV generator 105 directly. For this purpose, generator 116 may include any suitable mechanical coupling arrangement (e.g., levers and springs). Alternatively, generator 116 may be configured to convert mechanical movement of article 100 into storable elastic, electrical or other energy. Generator 116 may include any suitable mechanical and/or electromechanical converter arrangements (e.g., springs, coils, inductors, and magnets) for this purpose. The energy generated in this manner by generator 116 may be used either directly to drive UV generator 105, or stored for later use (e.g., in power source/receiver 113).

More generally, the operation of UV generator 105/article 100 may be supervised by a control device or system.

FIG. 4 shows an exemplary controller 107 configured to supervise operation of UV generator 105/article 100. Controller 107 may have any suitable mechanical or electromechanical structure, and include an optional programmable interface 114. In operation, controller 107 may control timing and amounts of UV energy delivered to contact region 101 in response to one or more event-triggered control signals. The event-triggered control signals may be generated by one or more control elements. The control elements may, for example, include one or more of sensor 109, timer 111, counter 112, or a user-activated switch (not shown). As noted previously, each of these control elements may be disposed either inside or outside article 100.

Sensor 109 may be a contact sensor which is configured to determine if a contact has been made to contact region 101 and to accordingly generate a control signal to activate UV generator 105 directly, or via controller 107, to provide UV energy across article 100 to contact region 101. The contact sensor may, for example, be any of a capacitive, a resistive, a thermal, a mechanical, a piezoelectric, an ultrasonic, an electromagnetic, or an optical sensor.

Additionally or alternatively, sensor 109 may be a proximity sensor arranged to determine if a contact to contact region 101 is likely, and to accordingly generate a control signal to activate UV generator 105 directly, or via controller 107, to provide UV energy to contact region 101 from within article 100. Like the contact sensor, the proximity sensor may, for example, be any of a capacitive, a resistive, a thermal, a mechanical, a piezoelectric, an ultrasonic, an electromagnetic, or an optical sensor.

Further, sensor 109 may be a bio-sensor arranged to determine a presence of biological materials (e.g., body fluids, mucins, sweat, lipids, etc.) on contact region 101, and to accordingly generate a control signal to activate UV generator 105 directly, or via controller 107, to provide UV energy to contact region 101 from within article 100. The bio-sensor for detecting a presence of biological materials may be any one of an optical sensor, a frustrated total internal reflection sensor, an ultrasonic sensor, a surface acoustic wave sensor, a surface plasmon resonance sensor, a resistive sensor, a capacitive sensor, and/or a chemical sensor.

FIGS. 2 and 4, for visual clarity, show a solitary sensor 109. However, it will be understood that any suitable numbers of sensors of various types may be deployed. Further, the sensor(s) may be configured to identify particular portions or sub regions of contact region 101 of interest, and to accordingly activate UV generator 105 directly, or via controller 107, to provide UV energy across article 100 only to those particular portions or subregions if so desired.

Control elements such as timer 111 or counter 112 also may generate alternate or additional event-triggered control signals to activate UV generator 105 only at certain times and/or only for particular durations. For example, counter 112, which may be an indexed or resettable counter, may count a number of contacts made, and activate UV generator 105 to provide UV energy each time the counted number equals or exceeds a predetermined number. Similarly, controller 107 may be coupled to timer 111, which clocks or times the provision of UV energy across article 100. Controller 107 may be further configured to respond to various sensor signals so that the provision of UV energy across article 100 begins a predetermined time interval after a contact is made, before a contact is made, or during a contact. In any case, the provision of UV energy may be continuous for a predetermined time interval after a triggering event.

Alternatively or additionally, controller 107 may be further configured to control the provision of UV energy across article 100 according to predetermined schedules. A predetermined schedule may be independent of the state or condition of contact region 101. For example, a predetermined schedule may ask for the provision of UV energy across article 100 every ten minutes, independent of the number of contacts made in the interim. Alternative predetermined schedules may be flexible or adjustable to take into consideration events, including without limitation, events potentially affecting contact region 101. For example, UV energy may be scheduled to be routinely released every ten minutes, but the schedule may be advanced or supplemented if a number of contacts made in the interim exceeds three. Similarly, timing or amount of release of UV energy may be responsive to a number of persons in a region proximate the contact region 101 or to other environmental events (e.g. changes in heating, ventilation, and air conditioning (HVAC) operation in the area or building). Moreover, the schedule, amount, or other aspects of release of UV energy may be controlled by controller 107 or other controller systems that may be located nearby or distant from contact region 101. In one approach, for example, the schedule, amount, or other aspects of release of the sterilizing UV energy may be controlled through a remote control system in a different building or facility, for example, through wireless, wired, IP protocol or other approaches.

The predetermined schedules and the responses of UV generator 105/controller 107 to various control signals may be set up or programmed by a user, for example, through programmable interface 114.

Article 100 also may include an optional status indicator 110, which is configured to indicate a state of the contact region and/or c UV generator 105. Status indicator 110 may, for example, include a set of red, yellow and green color light emitting diodes corresponding to various sterilization states of contact region 101 as determined by one or more sensors or control elements. Other versions of status indicator 110 may include other visual, audio, RF or electromagnetic and/or tactile displays of the state of contact region 101.

Figure 5:
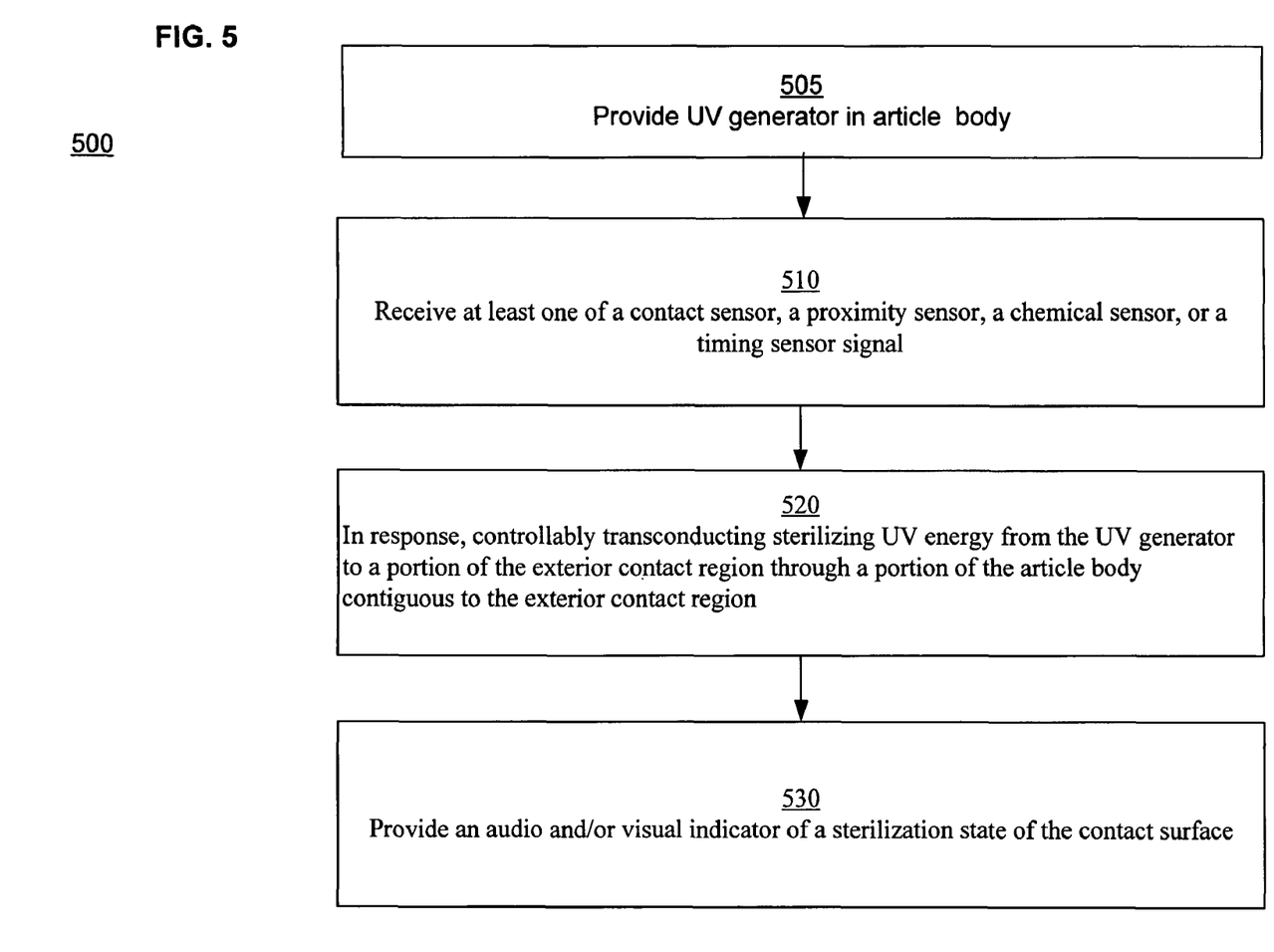
FIGS. 5 and 6 are flow diagrams illustrating exemplary methods for inhibiting the spread of germs by indirect contact, in accordance with the principles of the solutions described herein.
Figure 6:
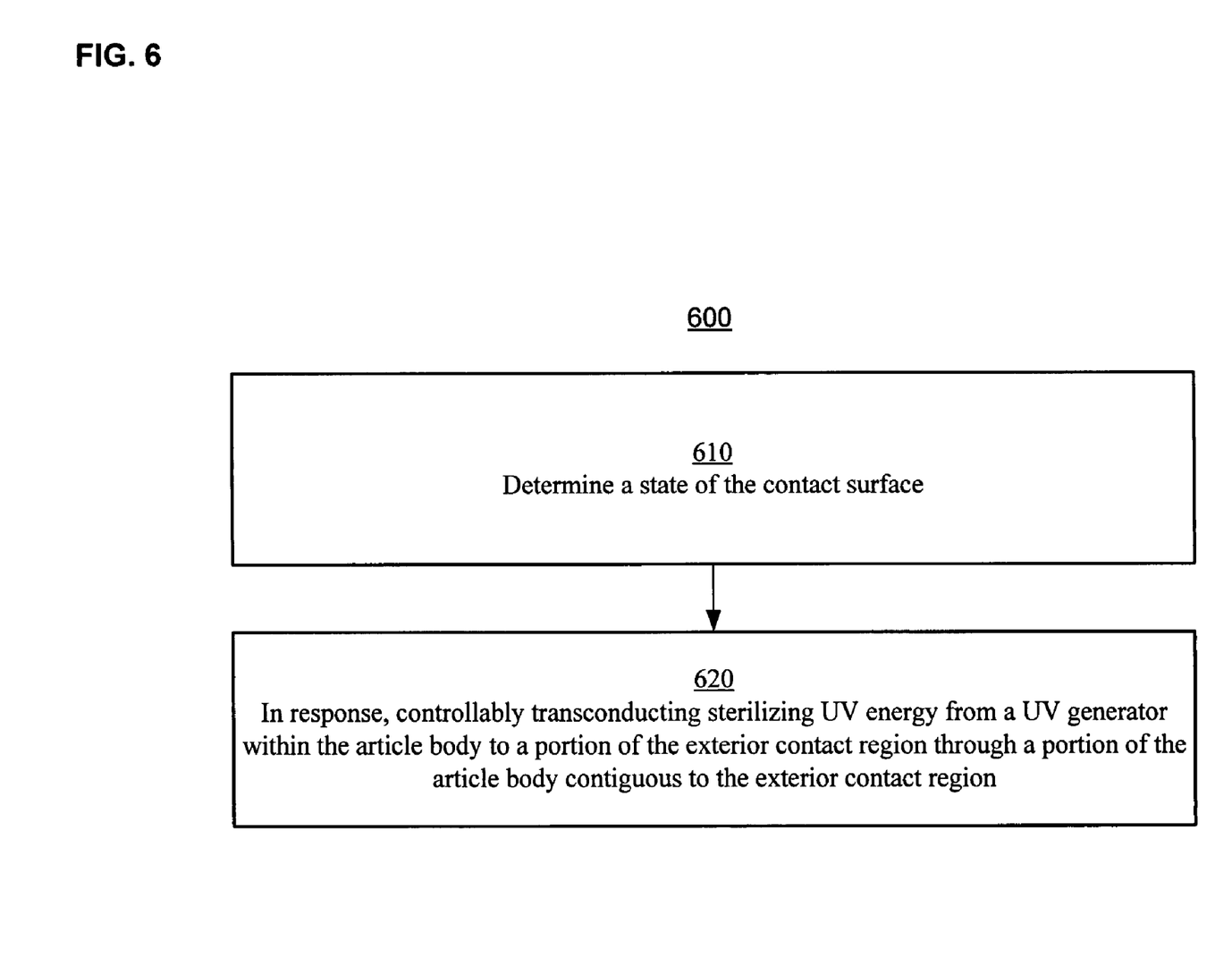

FIGS. 5 and 6 show exemplary features of methods for inhibiting germ transmission from contact regions on articles. The methods involve self-sterilization of the contact regions.

FIG. 5 shows a method 500 for sterilizing an exterior contact region disposed on an article, which includes a subsurface or interior region adjacent or contiguous to the exterior contact region. Method 500 includes: providing a UV generator in the article body (505); and in response to an event, controllably transconducting or flowing sterilizing UV energy from the UV generator to a portion of the exterior contact region through a portion of the article body contiguous to the exterior contact region (520).

The controllable flow of UV energy is initiated, sustained or terminated, in response to receiving at least one of a contact sensor, a proximity sensor, or a timing sensor signal (510). Method 500 also optionally includes displaying or indicating a status of the contact region (530).

FIG. 6 shows another method 600 for sterilizing an exterior contact region disposed on an article body. Method 600 includes determining a state of the contact region (610), and in response, controllably transconducting sterilizing UV energy from a UV generator within the article body to a portion of the exterior contact region through a portion of the article body contiguous to the exterior contact region (620). At least a portion of the contact region is sterilized by action of the sterilizing UV energy provided from within the article body.

In method 600, determining a state of the contact region (610) many include determining if a contact has been made to the contact region, or is likely to be made. Any suitable contact or proximity sensor may be used for this purpose. Additionally or alternatively, determining a state of the contact region (610) may involve determining if biological materials are present on the contact region by deploying a bio- or chemical sensor. The bio- or chemical sensor may be a surface plasmon resonance sensor.

Further, in method 600, controllably providing sterilizing UV energy from within the article body may occur according to a programmed routine or a predetermined schedule Controllably providing sterilizing UV energy from within the article body may include timing of the provision of the sterilizing UV energy across the article body, providing the sterilizing UV energy a predetermined time interval before, during or after a contact is made, providing the sterilizing UV energy after a predetermined number of contacts, and/or providing the sterilizing UV energy continuously for a predetermined time interval.

In method 600, contact-actuated power may be utilized to controllably generate and/or flow the sterilizing UV energy across the article body. The contact-actuated power may be generated by a movable mechanism, for example, a pressure-activated mechanism. Method 600 may further include storing contact-actuated power to controllably generate and/or flow the sterilizing UV energy across the interface at a later time.

Like method 500, method 600 also optionally includes displaying or indicating a status of the contact region. The display may be audio, visual, tactile or any combination thereof.

While various aspects and embodiments have been disclosed herein, other aspects and embodiments will be apparent to those skilled in the art. For example, controlled amounts of UV energy may be delivered to contact region 101 from within article 100, not merely in response to a sterilization state or condition of the contact region, but additionally or alternatively in response to movement or orientation of article 100 or portions thereof. Thus, a door knob may be self-sterilized in response to a door closing motion. Similarly, a tooth brush may be self-sterilized after it is picked up. A key may be self-sterilized after it is held in horizontal orientation as in a lock keyhole. Similarly, the tooth brush may be self-sterilized after it is placed vertically in a tooth-brush stand. Further, for example, UV generator 105/controller 107 may include a manual or automatic disable feature which overrides sterilizing schedules of article 100 in response to one or more external conditions. Delivery of UV energy to contact region 101 may be deemed unnecessary and accordingly disabled, for example, in response to contact or anticipated contact with specific individuals. Similarly, delivery of UV energy to contact region 101 may be deemed unnecessary and accordingly disabled in particular environmental conditions (e.g., for particular humidity or temperature levels) or when particular types of biological materials are present on contact region 101. As another example, article 100 may include a manual or automatically operated cover, which confines UV energy to the vicinity of contact region 101 to prevent unintended or inadvertent exposure of persons to the UV energy while contact region 101 is being sterilized.

It will be understood that the various aspects and embodiments disclosed herein are for purposes of illustration and are not intended to be limiting, with the true scope and spirit being indicated by the following claims.

The invention claimed is:

1. A method of sterilizing an exterior contact region disposed on an article body, the method comprising: providing a UV generator in the article body; providing a photonic crystal device for coupling UV energy generated by the UN generator to the contact region; and in response to an event, controllably transconducting sterilizing UV energy from the UV generator to a portion of the exterior contact region through a portion of the article body contiguous to the exterior contact region.

2. The method of claim 1, further comprising, providing a light-guiding structure to transport light from the UV generator to the contact region.

3. The method of claim 2, wherein providing a light-guiding structure comprises providing a structure configured to transport light from the UV generator to the contact region through an underlying surface region.

4. The method of claim 2, wherein providing a light-guiding structure comprises providing a structure configured to laterally transport light from the UV generator to the contact region along a surface of the article body.

5. The method of claim 1, further comprising, providing a plasmon-supporting structure for coupling UV energy generated by the UV generator to the contact region via plasmons.

6. The method of claim 1, further comprising, providing a total internal reflection device for coupling UV energy generated by the UV generator to the contact region.

7. The method of claim 1, wherein providing a UV generator comprises providing a UV generator with at least a portion thereof embedded in the contact region.

8. The method of claim 1, further comprising, providing a programmable mechanism configured to control provision of the sterilizing UV energy to the contact region.

9. The method of claim 1, further comprising, providing a user-activated switch configured to control provision of the sterilizing UV energy to the contact region according to a user command.

10. The method of claim 1, further comprising, providing sterilizing UV energy to the contact region a predetermined time interval after a contact has been made.

11. The method of claim 1, further comprising, providing sterilizing UV energy to the contact region before a contact is made.

12. The method of claim 1, further comprising, providing sterilizing UV energy to the contact region during a contact.

13. The method of claim 1, further comprising, providing a status indicator configured to indicate a sterilization state of the contact region.

14. The method of claim 13, wherein the status indicator is further configured to provide at least one of a tactile, an audio, an RF, and/or a visual display of the sterilization state of the contact region.

15. The method of claim 1, wherein the event is a signal from at least one of a contact sensor, a proximity sensor, or a timing sensor.

16. The method of claim 1, wherein providing the UV generator comprises providing a plasmon-enhanced extreme ultraviolet light source.

17. The method of claim 1, wherein the article body is configured as any one of a handle, a knob, a seat, a key board, a switch, a button, a computer mouse or control device, a desktop, a kitchen or bathroom surface, a working surface, a bus seat, a gymnasium equipment, a restaurant booth, a toy, a headphone, a telephone, an automatic teller machine, a vending machine, a shopping cart, a transportation vehicle device or fixture.

18. The method of claim 1, further comprising, providing any one of a capacitive, a resistive, a mechanical, a piezoelectric, a thermal, an ultrasonic, or an optical sensor configured to determine if a contact has been made to the contact region and to accordingly activate the UV generator to provide sterilizing UV energy to the contact region through the article body.

19. The method of claim 1, further comprising, providing a proximity sensor configured to determine if a contact to the contact region is imminent and to accordingly activate the UV generator to provide sterilizing UV energy to the contact region through the article body.

20. The method of claim 1, further comprising, providing a sensor configured to determine a presence of biological materials on the contact region and to accordingly activate the UV generator to provide sterilizing UV energy to the contact region through the article body.

21. The method of claim 20, wherein providing a sensor configured to determine a presence of biological materials comprises providing any one of an optical sensor, a frustrated total internal reflection sensor, an ultrasonic sensor, a surface acoustic wave sensor, a surface plasmon resonance sensor, a resistive sensor, a capacitive sensor, a biosensor, and/or a chemical sensor.

22. The method of claim 1, further comprising, providing a resettable counter configured to count a number of contacts and to activate the UV generator to provide sterilizing UV energy to the contact region when the number of contacts exceeds a predetermined number.

23. The method of claim 1, further comprising, providing a controller configured to control provision of the sterilizing UV energy to the contact region according to a predetermined schedule.

24. The method of claim 1, further comprising, providing a timer configured to time the provision of the sterilizing UV energy to the contact region.

25. The method of claim 1, further comprising, providing a contact-actuated power-generating mechanism configured to provide energy for operation of the UV generator.

26. The method of claim 25, wherein the contact-actuated power-generating mechanism is a movable mechanism.

27. The method of claim 25, wherein the contact-actuated power-generating mechanism is a pressure activated mechanism.

28. A method of sterilizing an article which has an article body and an exterior contact region disposed thereon, comprising: determining a state of the contact region; and in response to determining a state of the contact region, controllably transconducting sterilizing UV energy from the UV generator to a portion of the exterior contact region through a portion of the article contiguous to the exterior contact region, whereby at least a portion of the contact region is sterilized by action of the sterilizing UV energy, wherein controllably transconducting sterilizing UV energy comprises providing the sterilizing UV energy upon or after a predetermined number of contacts.

29. The method of claim 28, wherein determining a state of the contact region comprises determining if a contact has been made to the contact region.

30. The method of claim 28, wherein determining a state of the contact region comprises determining if a contact is proximate.

31. The method of claim 28, wherein determining a state of the contact region comprises determining if biological materials are present on the contact region.

32. The method of claim 28, wherein controllably transconducting sterilizing UV energy from the UV generator to a portion of the exterior contact region comprises providing the sterilizing UV energy according to a programmed routine.

33. The method of claim 28, wherein controllably transconducting sterilizing UV energy comprises providing the sterilizing UV energy according to a predetermined schedule.

34. The method of claim 28, wherein controllably transconducting sterilizing UV energy comprises providing the sterilizing UV energy a predetermined time interval after a contact is made.

35. The method of claim 28, wherein controllably transconducting sterilizing UV energy comprises providing the sterilizing UV energy before a contact is made.

36. The method of claim 28, wherein controllably transconducting sterilizing UV energy comprises providing the sterilizing UV energy during a contact.

37. The method of claim 28, wherein controllably transconducting sterilizing UV energy comprises generating the sterilizing UV energy internally in the article.

38. The method of claim 28, further comprising, providing a status indicator configured to indicate a sterilization state of the contact region.

39. The method of claim 38, wherein the status indicator is further configured to provide at least one of a tactile, an audio, an RF, and/or a visual display of the sterilization state of the contact region.

40. The method of claim 29, wherein determining if a contact has been made or proximate comprises deploying any one of a capacitive, a resistive, a mechanical, a piezoelectric, a thermal, an ultrasound, or an optical contact sensor.

41. The method of claim 28, wherein controllably transconducting sterilizing UV energy comprises providing the sterilizing UV energy in response to a user command.

42. The method of claim 28, further comprising resetting a count of the number of contacts after providing the sterilizing UV energy.

43. The method of claim 28, wherein controllably transconducting sterilizing UV energy comprises timing the provision of the sterilizing UV energy.

44. The method of claim 28, wherein controllably transconducting sterilizing UV energy comprises providing the sterilizing UV energy a predetermined time interval after a previous provision.

45. The method of claim 28, wherein controllably transconducting sterilizing UV energy comprises providing the sterilizing UV energy continuously for a predetermined time interval.

46. The method of claim 28, further comprising, providing a UV generator in the article body.

47. The method of claim 46, wherein providing the UV generator comprises providing a plasmon-enhanced extreme ultraviolet light source.

48. The method of claim 46, wherein providing a UV generator comprises providing a UV generator with at least a portion thereof embedded in the contact region.

49. The method of claim 28, further comprising, providing a light-guiding structure to transport light to the contact region through an underlying surface region.

50. The method of claim 49, wherein providing a light-guiding structure comprises providing one of a structure configured to transport light to the contact region laterally along a surface of the article body, a plasmon-supporting structure for coupling UV energy to the contact region via plasmons, a total internal reflection device for coupling UV energy to the contact region, and/or a photonic crystal device for coupling UV energy to the contact region.

51. The method of claim 28, further comprising, providing a programmable mechanism and/or a timer configured to control provision of the sterilizing UV energy to the contact region.

52. The method of claim 28, further comprising, providing a contact-actuated power-generating mechanism configured to provide energy for operation of the UV generator.

53. The method of claim 52, wherein the contact-actuated power-generating mechanism is a pressure activated mechanism.

54. The method of claim 52, further comprising, providing an energy storage device configured to store power generated by the power-generating mechanism.

* * * * *